(12) United States Patent
Gower et al.

(10) Patent No.: US 11,065,246 B2
(45) Date of Patent: Jul. 20, 2021

(54) GLUCOMANNAN CONTAINING PHARMACEUTICAL COMPOSITIONS WITH EXTENDED RELEASE AND ABUSE DETERRENT PROPERTIES

(71) Applicant: SpecGX LLC, Webster Groves, MO (US)

(72) Inventors: Brad L. Gower, Hazelwood, MO (US); Jae Han Park, Hazelwood, MO (US); Clifford J. Herman, Hazelwood, MO (US); Tsz Chung Lai, Hazelwood, MO (US); Kai Feng, Hazelwood, MO (US)

(73) Assignee: SpecGX LLC, Webster Groves, MO (US)

( * ) Notice: Subject to any disclaimer, the term of this patent is extended or adjusted under 35 U.S.C. 154(b) by 0 days.

(21) Appl. No.: 15/417,541

(22) Filed: Jan. 27, 2017

(65) Prior Publication Data

US 2017/0224826 A1    Aug. 10, 2017

Related U.S. Application Data

(60) Provisional application No. 62/292,463, filed on Feb. 8, 2016.

(51) Int. Cl.
| | | |
|---|---|---|
| *A61K 31/485* | (2006.01) | |
| *A61K 9/20* | (2006.01) | |
| *A61K 47/10* | (2017.01) | |
| *A61K 47/36* | (2006.01) | |

(52) U.S. Cl.
CPC ............ *A61K 31/485* (2013.01); *A61K 9/205* (2013.01); *A61K 9/2013* (2013.01); *A61K 9/2031* (2013.01); *A61K 9/2054* (2013.01); *A61K 47/10* (2013.01); *A61K 47/36* (2013.01)

(58) Field of Classification Search
None
See application file for complete search history.

(56) References Cited

U.S. PATENT DOCUMENTS

| | | |
|---|---|---|
| 6,488,963 B1 | 12/2002 | McGinity et al. |
| 8,075,872 B2 | 12/2011 | Arkenau-Maric et al. |
| 8,114,383 B2 | 2/2012 | Bartholomaus et al. |
| 8,173,152 B2 | 5/2012 | Crowley et al. |
| 8,192,722 B2 | 6/2012 | Arkenau-Maric et al. |
| 8,309,060 B2 | 11/2012 | Bartholomaus et al. |
| 8,894,987 B2 | 11/2014 | McKenna et al. |
| 8,894,988 B2 | 11/2014 | McKenna et al. |
| 8,911,719 B2 | 12/2014 | McKenna et al. |
| 9,044,402 B2 | 6/2015 | Tygesen et al. |
| 9,060,976 B2 | 6/2015 | Wright et al. |
| 9,084,816 B2 | 7/2015 | McKenna et al. |
| 9,095,615 B2 | 8/2015 | McKenna et al. |
| 2013/0280176 A1 | 10/2013 | Diezi |
| 2013/0280177 A1 | 10/2013 | Raman et al. |
| 2014/0010873 A1 | 1/2014 | Tygesen et al. |
| 2014/0017310 A1 | 1/2014 | Gower et al. |
| 2015/0250886 A1 | 9/2015 | Bhandari et al. |
| 2016/0000703 A1 | 1/2016 | Micka et al. |

FOREIGN PATENT DOCUMENTS

| | | | |
|---|---|---|---|
| EP | 1897545 | 12/2008 | |
| WO | 03/033031 A1 | 4/2003 | |
| WO | 2013/077851 A1 | 5/2013 | |
| WO | WO-2014047731 A1 * | 4/2014 | ............ A61K 9/205 |
| WO | 2014/152296 A1 | 9/2014 | |
| WO | 2014/190440 A1 | 12/2014 | |
| WO | 2017/139106 A1 | 8/2017 | |

OTHER PUBLICATIONS

International Search Report and Written Opinion from related International Application No. PCT/US2017/15235, dated Apr. 21, 2017; 10 pgs.
Extended European Search Report from related European Application No. EP 15815497.1, dated Nov. 7, 2017; 7 pgs.
European Search Report dated Jul. 26, 2019 in related EP Application No. 17750563.3, 5 pp.
Examination report dated Oct. 13, 2020 from related EP Application No. 17750563.3, 2 pgs.
Office action dated Aug. 13, 2020 from related MX Application No. MX/a/2018/008868, 4 pgs.
Office action dated Sep. 25, 2020 from related JP Application No. 2018-536818, 7 pgs.

* cited by examiner

*Primary Examiner* — Bethany P Barham
*Assistant Examiner* — Barbara S Frazier

(57) ABSTRACT

A pharmaceutical composition comprising at least one active pharmaceutical ingredient (API) or a pharmaceutically acceptable salt thereof, a glucomannan, a first polyalkylene oxide having an average molecular weight of no more than 300,000, and a second polyalkylene oxide having an average molecular weight of at least 1,000,000 and methods of making. The pharmaceutical composition provides extended release of the API and has abuse deterrent features.

18 Claims, No Drawings

GLUCOMANNAN CONTAINING PHARMACEUTICAL COMPOSITIONS WITH EXTENDED RELEASE AND ABUSE DETERRENT PROPERTIES

CROSS-REFERENCE TO RELATED APPLICATIONS

This application claims the priority of U.S. Provisional Application Ser. No. 62/292,463, filed Feb. 8, 2016, the disclosure of which is hereby incorporated by reference in its entirety.

FIELD OF THE INVENTION

The present disclosure generally relates to pharmaceutical compositions that provide extended release of active ingredients and have abuse deterrent properties.

BACKGROUND OF THE INVENTION

The misuse of pain relievers represents a majority of the overall problem of prescription drug abuse. The abuse of painkillers mirrors the increasing availability of opioid dosage forms due to the more aggressive treatment of chronic pain in the populace. The increasing number of abusers, increasing availability, and the destructive/addictive potential of opiates make prescription pharmaceutical abuse a matter of public health concern.

Several routes of administration are commonly attempted by abusers. For example, the pharmaceutical dosage form may be chewed, or it may be crushed or pulverized into a powder and administered intranasally (i.e., snorted). Alternatively, the intact or tampered pharmaceutical dosage form may be dissolved in a suitable solvent and administered parenterally (i.e., injected intravenously), or the intact or tampered dosage form may be smoked.

To deter misuse and/or abuse of pharmaceutical dosage forms with extended drug release, multiple strategies have been employed. One approach is to include an opioid antagonist in opioid pharmaceutical dosage forms. The opioid antagonist, which is not orally active, will substantially block the analgesic effects of the opioid when one attempts to abuse the tampered dosage form via snorting or injecting. Another approach it to include aversive and/or bitter agents in pharmaceutical formulations to prevent abuse of the active pharmaceutical ingredient. This approach, however, could cause adverse effects in the patient population due to the properties associated with these agents. Lastly, a safer alternative is to incorporate excipients that provide a physical barrier in which abuse of the API is deterred. In one case, this is accomplished by incorporating the API into a polymeric matrix tablet containing high molecular weight gel forming polymers such as polyethylene oxide. The polymeric matrix tablet has increased hardness and retains a plastic-like nature after curing at a temperature above the softening temperature of the polyethylene oxide. The resultant tablet dosage form is difficult to crush or chew and forms a viscous gel when the dosage form comes into contact with a suitable solvent. However, because polyethylene oxide forms oxidative peroxide radicals when heated, APIs susceptible to oxidative degradation should be incorporated into such dosage forms with care. Alternately, the conditions for curing the dosage form with an API sensitive to oxidation must be tightly controlled, sometimes limiting the tamper resistant properties thereof. Similarly, thermolabile APIs cannot be incorporated into these cured dosage forms.

Thus, there is a need for additional pharmaceutical dosage forms comprising polymers that provide extended release of the API and that are resistant to abuse and/or misuse.

SUMMARY OF THE INVENTION

The present disclosure provides abuse deterrent, extended release pharmaceutical compositions comprising glucomannan.

One aspect of the present disclosure encompasses a solid dosage form comprising at least one active pharmaceutical ingredient (API) or a pharmaceutically acceptable salt thereof, a glucomannan, a polyalkylene oxide having an average molecular weight of no more than about 300,000 Daltons, and a second polyethylene oxide having an average molecular weight of at least 1,000,000 Daltons.

Another aspect of the present disclosure provides a process for preparing the solid dosage form of the disclosure. The process comprises forming a mixture comprising the API, the glucomannan, the first and second polyalkylene oxides, and optionally one or more pharmaceutically acceptable excipients, forming the mixture into a solid dosage unit; and heating the solid dosage unit to form the solid dosage form.

Other aspects and iterations of the disclosure are described in more detail below.

DETAILED DESCRIPTION OF THE INVENTION

The present disclosure provides pharmaceutical compositions that provide extended release of an active pharmaceutical ingredient and have abuse deterrent properties. The pharmaceutical composition comprises at least one active pharmaceutical ingredient (API) or a pharmaceutically acceptable salt thereof, at least one natural gum, at least one polyalkylene oxide having an average molecular weight of no more than about 300,000, and at least one polyalkylene oxide having an average molecular weight of at least 1,000,000. The composition deters abuse by breaking into a plurality of particles having an average diameter of greater than about 250 microns when crushed, ground, or pulverized, and by forming a viscous gel when contacted with about 10 mL or less of an aqueous solution.

(I) Pharmaceutical Composition

One aspect of the present disclosure provides extended release, abuse deterrent pharmaceutical compositions. Detailed below are the components of the composition, dosage forms of the composition, release characteristics of the composition, and abuse deterrent properties of the composition.

(a) Components of the Composition

The pharmaceutical composition disclosed herein comprises at least one natural gum, at least one polyalkylene oxide having an average molecular weight of no more than 300,000, at least one polyalkylene oxide having an average molecular weight of at least 1,000,000, and at least one active pharmaceutical ingredient (API) or a pharmaceutically acceptable salt thereof. This combination of polymers creates a functional abuse deterrent composition that provides extended release of the API.

(i) Natural Gums

The pharmaceutical composition discloses herein comprises at least one natural gum. Natural gums are noncellulose polysaccharides derived from botanical sources, seaweeds, or produced via bacterial fermentation. Natural gums are water-soluble and/or water-swellable polymers that are capable of forming highly viscous gels even at low concentrations. Non-limiting examples of plant-derived natural gums include glucomannan, *albizia* gum, aloe mucilage, beta-glucan, chicle gum, dammar gum, fenugreek gum, guar gum, gum arabic (also called acacia gum), gum copal, gum ghatti, gum tragacanth, hakea gum, *Hibiscus rosasinensis* gum, honey locust gum, hupu gum, karaya gum, khaya gum, *Lepidium sativum* gum, locust bean gum, mastic gum, *Mimosa scabrella* gum, *Mimosa pudica* gum, okra gum, *psyllium* seed husks (also called ispaghula husk), spruce gum, *Sterculia foetida* gum, tamarind gum, tara gum, and derivatives of any of the foregoing. Examples of natural gums derived from seaweeds include, without limit, alginate or alginic acid, fucoidan, and laminarin derived from brown seaweeds, and agar and carrageenans derived from red seaweeds. Non-limiting examples of natural gums produced by bacterial fermentation include xanthan gum, gellan gum, dextran, welan gum, diutan gum, pullulan, and derivatives thereof.

In specific embodiments, the natural gum may be a glucomannan. Glucomannans are linear polysaccharides composed of β-1,4 linked D-mannose and D-glucose residues (with acetyl side branches on some of the backbone units) that are derived from softwoods, roots, tubers, and plant bulbs. The mannose to glucose ratio depends upon the source of the glucomannan. For example, glucomannan derived from the tubers of *Amorphophallus konjac* has a mannose:glucose ratio of 1.6:1, whereas glucomannans extracted from Scotch pine or orchids have ratios of 2.1:1 or 3.6:1, respectively. In various embodiments, the glucomannan may be derived from *Amorphophallus konjac*, *Bletilla striata*, *Cyrtopodium andersonii*, *Orchis mureo*, *Aloe vera*, or *Pinus sylvestris*. In certain embodiments, the degree of acetylation of the glucomannan may be increased or decreased via suitable chemical reactions. In exemplary embodiments, the glucomannan may be derived from *Amorphophallus konjac* K. Koch (also known as konjac glucomannan).

In general, the natural gum has a high molecular weight and forms a viscous mixture or gel upon contact with water or an aqueous solution. The molecular weight distribution of natural gums can range from about 200,000 to about 20,000,000. In some embodiments, the natural gum may be a glucomannan having an average molecular weight of greater than about 200,000, greater than about 500,000, greater than about 1,000,000, greater than about 2,000,000, or greater than about 4,000,000.

The amount of the natural gum present in the pharmaceutical composition, can and will vary depending upon the desired properties of the pharmaceutical composition, as well as the identity and amounts of other components present in the composition. In general, the amount of natural gum in the composition may range from about 2% to about 60% by weight of the pharmaceutical composition. In various embodiments, the amount of the natural gum may range from about 5% to about 50% or from about 10% to about 35% by weight of the pharmaceutical composition. In one specific embodiment, the amount of natural gum in the composition may range from about 10% to about 20% by weight of the pharmaceutical composition. In another specific embodiment, the amount of natural gum in the composition may range from about 20% to about 30% by weight of the pharmaceutical composition.

(ii) Polyalkylene Oxides

The pharmaceutical composition discloses herein at least two polyalkylene oxides that have different molecular weights. In particular, the composition comprises a first polyalkylene oxide having an average molecular weight of no more than about 300,000, and a second polyalkylene oxide having an average molecular weight of at least 1,000,000. The low molecular weight polyalkylene oxide generally functions as a diluent and/or imparts thermoplasticity to the composition, and the high molecular weight polyalkylene oxide generally functions as a gelling agent and/or controlled release polymer in the composition.

First Polyalkylene Oxide.

The first polyalkylene oxide having an average molecular weight of no more than about 300,000 may be a polyethylene oxide, a polymethylene oxide, a polypropylene oxide, or a copolymer thereof. In exemplary embodiments, the first polyalkylene oxide is a polyethylene oxide. In some embodiments, the first polyalkylene oxide, which may be polyethylene oxide, has an average molecular weight of about 300,000. In other embodiments, the first polyalkylene oxide, which may be polyethylene oxide, has an average molecular weight of about 200,000. In specific embodiments, the first polyalkylene oxide, which may be polyethylene oxide, has an average molecular weight of about 100,000.

The amount of first polyalkylene oxide present in the pharmaceutical composition can and will vary depending upon the identity/amount of the second polyalkylene oxide, the identity/amount of the natural gum, and/or the other components utilized in the pharmaceutical composition. In general, the amount of the first polyalkylene oxide present in the pharmaceutical composition may range from about 10% to about 70% by weight of the composition. In various embodiments, the amount of the first polyalkylene oxide present in the pharmaceutical composition may range from about 20% to about 60%, from about 30% to about 50%, or from about 35% to about 45% by weight of the pharmaceutical composition.

Second Polyalkylene Oxide.

The second polyalkylene oxide having an average molecular weight of at least 1,000,000 may be a polyethylene oxide, a polymethylene oxide, a polypropylene oxide, or a copolymer thereof. In exemplary embodiments, the second polyalkylene oxide is a polyethylene oxide. In some embodiments, the second polyalkylene oxide, which may be polyethylene oxide, has an average molecular weight of about 2,000,000. In other embodiments, the second polyalkylene oxide, which may be polyethylene oxide, has an average molecular weight of about 4,000,000. In further embodiments, the second polyalkylene oxide, which may be polyethylene oxide, has an average molecular weight of about 5,000,000. In still other embodiments, the second polyalkylene oxide, which may be polyethylene oxide, has an average molecular weight of about 7,000,000. In additional embodiments, the second polyalkylene oxide, which may be polyethylene oxide, has an average molecular weight of about 8000,000. In other embodiments, the second polyalkylene oxide, which may be polyethylene oxide, has an average molecular weight of about 15,000,000.

The amount of second polyalkylene oxide present in the pharmaceutical composition can and will vary depending upon the identity/amount of the first polyalkylene oxide, the identity/amount of the natural gum, and/or the other components utilized in the pharmaceutical composition. In general, the amount of the second polyalkylene oxide present in the pharmaceutical composition may range from about 5% to about 30% by weight of the composition. In certain embodiments, the amount of the second polyalkylene oxide present in the pharmaceutical composition may range from about 7% to about 27%, or from about 8% to about 25% by weight of the pharmaceutical composition. In one embodiment, the amount of the second polyalkylene oxide present in the pharmaceutical composition may range from about 9% to about 11% by weight of the pharmaceutical composition. In another embodiment, the amount of the second polyalkylene oxide present in the pharmaceutical composition may range from about 18% to about 24% by weight of the pharmaceutical composition.

(iii) Hydrophilic Gelling Polymer

In some embodiments, the pharmaceutical composition disclosed herein may also comprise at least one hydrophilic gelling polymer. The term "hydrophilic gelling polymer" refers to a polymer with affinity for water such that it readily absorbs water or an aqueous solution and/or swells when in contact with water or an aqueous solution to form a viscous mixture or gel.

A variety of hydrophilic gelling polymers are suitable for use in the pharmaceutical compositions disclosed herein. The polymer may be natural, semi-synthetic, or synthetic. Non-limiting examples of suitable hydrophilic gelling polymers include cellulose ethers, polyalkylene oxides, polyacrylic acids, polyamines, polyolefinic alcohols, polyvinyl lactams, derivatives thereof, and combinations thereof.

In some embodiments, the hydrophilic gelling polymer may be a cellulose ether. Cellulose ethers are cellulose derivatives in which the hydrogen atoms of hydroxyl groups are replaced with alkyl groups. The degree of substitution can and will vary. Non-limiting examples of suitable cellulose ethers include hydroxypropylcellulose (HPC), hydroxypropylmethylcellulose (HPMC), carboxymethylcellulose (CMC) (e.g., sodium carboxymethylcellulose), methylcellulose, hydroxyethylcellulose, hydroxyethylmethylcellulose, methylhydroxyethylcellulose, and the like. In specific embodiments, the cellulose ether may be hydroxypropylmethylcellulose, hydroxypropylcellulose, or combinations thereof. The cellulose ether may be a high viscosity grade. The average molecular weight of the cellulose ether may range from about 20,000 to about 1,500,000. In various embodiments, the weight average molecular weight of the cellulose ether may be about 30,000, about 90,000, about 100,000, about 120,000, about 250,000, about 850,000, or about 1,150,000.

In other embodiments, the hydrophilic gelling polymer may be a polyacrylic acid. Suitable polyacrylic acids include carbomers, which are homopolymers of acrylic acid cross linked with polyalcohol allyl ethers (e.g., allyl ether pentaerythritol, allyl ether of sucrose, or allyl ether of propylene), and polycarbophil, which is a homopolymer of acrylic acid cross linked with divinyl glycol. Available carbomers include Carbopol 910, 934, 940, 941, and 943P (the codes are indicators of molecular weight and the specific components of the polymer).

In additional embodiments, the hydrophilic gelling polymer may be a polyamine such as polyethyleneimine, polyvinylamine, or the like. In still further embodiments, the hydrophilic gelling polymer may be a polyolefinic alcohol (such as polyvinyl alcohol), or a polyvinyl lactam (such as, e.g., polyvinylpyrrolidone, polyvinyl caprolactam, and the like). The average molecular weight of said polymers may range from about 20,000 to about 1,300,000.

The amount of the hydrophilic gelling polymer present in the pharmaceutical composition can and will vary depending upon the desired properties of the pharmaceutical composition, as well as the identity and amounts of other components utilized in the pharmaceutical composition. In general, the amount of the hydrophilic gelling polymer may range from about 2% to about 50% by weight of the pharmaceutical composition. In various embodiments, the amount of the hydrophilic gelling polymer in the composition may range from about 3% to about 40%, from about 4% to about 30%, or from about 5% to about 20% by weight of the pharmaceutical composition.

(iv) Antioxidants

The pharmaceutical compositions disclosed herein may also further comprise at least one antioxidant. In general, the antioxidant is included to inhibit oxidation of oxidation sensitive APIs.

A variety of antioxidants are suitable for use in the pharmaceutical compositions disclosed herein. Non-limiting examples of suitable antioxidants include alpha-tocopherol, ascorbic acid, ascorbyl palmitate, butylated hydroxytoluene (BHT), butylated hydroxyanisole, citric acid, dihydroguaretic acid, ethylenediaminetetraacetic acid, potassium ascorbate, potassium sorbate, potassium metabisulfite, propylgallate, sodium bisulfate, sodium isoascorbate, sodium metabisulfite, sodium thiosulfate, sorbic acid, and 3,4-dihydroybenzoic acid.

In embodiments in which an antioxidant is included in the pharmaceutical composition, the amount of the antioxidant may range from about 0.01% to about 5% by weight of the pharmaceutical composition. In various embodiments, the amount of the antioxidant may range from about 0.01% to about 0.03%, from about 0.03% to about 0.1%, from about 0.1% to about 0.3%, from about 0.3% to about 1.0%, from about 1.0% to about 3.0%, or from about 3.0% to about 5.0% by weight of the pharmaceutical composition.

(v) Lubricants

The pharmaceutical compositions disclosed herein may also further comprise at least one lubricant, which facilitates preparation of solid dosage forms of the pharmaceutical composition. Non-limiting examples of suitable lubricants include magnesium stearate, calcium stearate, zinc stearate, colloidal silicon dioxide, hydrogenated vegetable oils, sterotex, polyoxyethylene monostearate, polyethylene glycol, sodium stearyl fumarate, sodium benzoate, sodium lauryl sulfate, magnesium lauryl sulfate, and light mineral oil. In exemplary embodiments, the lubricant may be magnesium stearate.

In embodiments in which the lubricant is included in the pharmaceutical composition, the amount of the lubricant may range from about 0.1% to about 3% by weight of the pharmaceutical composition. In various embodiments, the amount of the lubricant may range from about 0.1% to about 0.3%, from about 0.3% to about 1%, or from about 1% to about 3% by weight of the pharmaceutical composition. In exemplary embodiments, the amount of the lubricant may be about 1% by weight of the pharmaceutical composition.

(vi) Plasticizers

In some embodiment, the pharmaceutical composition also may contain a plasticizer to plasticize the polymers (e.g., polyalkylene oxides) in the composition. Non-limiting examples of suitable plasticizers that can be included in the composition include vitamin E succinate, vitamin E palmitate, vitamin E acetate, tocopherol terephthalate, ascorbyl palmitate, glycerol, polyethylene glycols, triethyl citrate, tributyl citrate, acetyl triethyl citrate, triacetin, dibutyl sebacate, diethyl phthalate, dibutyl phthalate, organic acids (e.g., citric acid, glutaric acid, malic acid, tartaric acid, and the like), sugar alcohols (e.g., sorbitol, xylitol, maltitol, and the like.), or mixtures of any of the foregoing. In exemplary embodiments, the plasticizer may be vitamin E succinate.

In embodiments in which the plasticizer is included in the pharmaceutical composition, the amount of the plasticizer may range from about 0.1% to about 5% by weight of the pharmaceutical composition. In various embodiments, the amount of the plasticizer may range from about 0.1% to about 0.3%, from about 0.3% to about 1%, from about 1.0% to about 3.0%, or from about 3.0% to about 5.0% by weight of the pharmaceutical composition.

(vii) APIs

The pharmaceutical composition disclosed herein comprises at least one API or a pharmaceutically acceptable salt thereof. Suitable APIs include, without limit, opioid analgesic agents (e.g., adulmine, alfentanil, allocryptopine, allylprodine, alphaprodine, anileridine, aporphine, benzylmorphine, berberine, bicuculine, bicucine, bezitramide, buprenorphine, bulbocaprine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphine, nalmefene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, and tramadol); opioid antagonists (e.g., naloxone, naltrexone, alvimopan, cyprodime, diprenorphine, gemazocine, 5'-guanidinonaltrindole, levallorphan, methylnaltrexone, naldemedine, nalmexone, nalorphine, naloxazone, naloxol, naloxonazine, 6β-naltrexol-d4, naltriben, naltrindole, norbinaltorphimine, oxilorphan, quadazocine, and samidorphan); non-opioid analgesic agents (e.g., acetylsalicylic acid, acetaminophen, paracetamol, ibuprofen, ketoprofen, indomethacin, diflunisol, naproxen, ketorolac, dichlophenac, tolmetin, sulindac, phenacetin, piroxicam, and mefamanic acid); anti-inflammatory agents (e.g., glucocorticoids such as alclometasone, fluocinonide, methylprednisolone, triamcinolone and dexamethasone; non-steroidal anti-inflammatory agents such as celecoxib, deracoxib, ketoprofen, lumiracoxib, meloxicam, parecoxib, rofecoxib, and valdecoxib); antitussive agents (e.g., dextromethorphan, codeine, hydrocodone, caramiphen, carbetapentane, and dextromethorphan); antipyretic agents (e.g., acetylsalicylic acid and acetaminophen); antibiotic agents (e.g., aminoglycosides such as, amikacin, gentamicin, kanamycin, neomycin, netilmicin, streptomycin, and tobramycin; carbecephem such as loracarbef; carbapenems such as certapenem, imipenem, and meropenem; cephalosporins such as cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; macrolides such as azithromycin, clarithromycin, dirithromycin, erythromycin, and troleandomycin; monobactam; penicillins such as amoxicillin, ampicillin, carbenicillin, cloxacillin, dicloxacillin, nafcillin, oxacillin, penicillin G, penicillin V, piperacillin, and ticarcillin; polypeptides such as bacitracin, colistin, and polymyxin B; quinolones such as ciprofloxacin, enoxacin, gatifloxacin, levofloxacin, lomefloxacin, moxifloxacin, norfloxacin, ofloxacin, and trovafloxacin; sulfonamides such as mafenide, sulfacetamide, sulfamethizole, sulfasalazine, sulfisoxazole, and trimethoprim-sulfamethoxazole; tetracyclines such as demeclocycline, doxycycline, minocycline, and oxytetracycline); antimicrobial agents (e.g., ketoconazole, amoxicillin, cephalexin, miconazole, econazole, acyclovir, and nelfinavir); antiviral agents (e.g., acyclovir, gangciclovir, oseltamivir, and relenza); steroids (e.g., estradiol, testosterone, cortisol, aldosterone, prednisone, and cortisone); amphetamine stimulant agents (e.g., amphetamine and amphetamine-like drugs); non-amphetamine stimulant agents (e.g., methylphenidate, nicotine, and caffeine); laxative agents (e.g., bisacodyl, casanthranol, *senna*, and castor oil); anti-nausea agents (e.g., dolasetron, granisetron, ondansetron, tropisetron, meclizine, and cyclizine); anorexic agents (e.g., fenfluramine, dexfenfluramine, mazindol, phentermine, and aminorex); antihistaminic agents (e.g., phencarol, cetirizine, cinnarizine, ethamidindole, azatadine, brompheniramine, hydroxyzine, and chlorpheniramine); antiasthmatic agents (e.g., zileuton, montelukast, omalizumab, fluticasone, and zafirlukast); antidiuretic agents (e.g., desmopressin, vasopressin, and lypressin); anti-migraine agents (e.g., naratriptan, frovatriptan, eletriptan, dihydroergotamine, zolmitriptan, almotriptan, and sumatriptan); antispasmodic agents (e.g., dicyclomine, hyoscyamine, and peppermint oil); antidiabetic agents (e.g., methformin, acarbose, miglitol, pioglitazone, rosiglitazone, nateglinide, repaglinide, mitiglinide, saxagliptin, sitagliptine, vildagliptin, acetohexamide, chlorpropamide, gliclazide, glimepiride, glipizide, glyburide, tolazamide, and tolbutamide); respiratory agents (e.g., albuterol, ephedrine, metaproterenol, and terbutaline); sympathomimetic agents (e.g., pseudoephedrine, phenylephrine, phenylpropanolamine, epinephrine, norepinephrine, dopamine, and ephedrine); H2 blocking agents (e.g., cimetidine, famotidine, nizatidine, and ranitidine); antihyperlipidemic agents (e.g., clofibrate, cholestyramine, colestipol, fluvastatin, atorvastatin, genfibrozil, lovastatin, niacin, pravastatin, fenofibrate, colesevelam, and simvastatin); antihypercholesterol agents (e.g., lovastatin, simvastatin, pravastatin, fluvastatin, atorvastatin, cholestyramine, colestipol, colesevelam, nicotinic acid, gemfibrozil, and ezetimibe); cardiotonic agents (e.g., *digitalis*, ubidecarenone, and dopamine); vasodilating agents (e.g., nitroglycerin, captopril, dihydralazine, diltiazem, and isosorbide dinitrate); vasoconstricting agents (e.g., dihydroergotoxine and dihydroergotamine); anticoagulants (e.g., warfarin, heparin, and Factor Xa inhibitors); sedative agents (e.g., amobarbital, pentobarbital, secobarbital, clomethiazole, diphenhydramine hydrochloride, and alprazolam); hypnotic agents (e.g., zaleplon, zolpidem, eszopiclone, zopiclone, chloral hydrate, and clomethiazole); anticonvulsant agents (e.g., lamitrogene, oxycarbamezine, phenytoin, mephenytoin, ethosuximide, methsuccimide, carbamazepine, valproic acid, gabapentin, topiramate, felbamate, and phenobarbital); muscle relaxing agents (e.g., baclofen, carisoprodol, chlorzoxazone, cyclobenzaprine, dantrolene sodium, metaxalone, orphenadrine, pancuronium bromide, and tizanidine); antipsychotic agents (e.g., phenothiazine, chlorpromazine, fluphenazine, perphenazine, prochlorperazine, thioridazine, trifluoperazine, haloperidol, droperidol, pimozide, clozapine, olanzapine, risperidone, quetiapine, ziprasidone, melperone, and paliperidone); antianxiolitic agents (e.g., lorazepam, alprazolam, clonazepam, diazepam, buspirone, meprobamate, and flunitrazepam); antihyperactive agents (e.g., methylphenidate, amphetamine, and dextroamphetamine); antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril); anti-neoplasia agents (e.g., taxol, actinomycin, bleomycin A2, mitomycin C, daunorubicin, doxorubicin, epirubicin, idarubicin, and mitoxantrone); soporific agents (e.g., zolpidem tartrate, eszopiclone, ramelteon, and zaleplon); tranquilizer agents (e.g., alprazolam, clonazepam, diazepam, flunitrazepam, lorazepam, triazolam, chlorpromazine, fluphenazine, haloperidol, loxapine succinate, perphenazine, prochlorperazine, thiothixene, and trifluoperazine); decongestant agents (e.g., ephedrine, phenylephrine, naphazoline, and tetrahydrozoline); beta blockers (e.g., levobunolol, pindolol, timolol maleate, bisoprolol, carvedilol, and butoxamine); alpha blockers (e.g., doxazosin, prazosin, phenoxybenzamine, phentolamine, tamsulosin, alfuzosin, and terazosin); non-steroidal hormones (e.g., corticotropin, vasopressin, oxytocin, insulin, oxendolone, thyroid hormone, and adrenal hormone); erectile disfunction improvement agents; herbal agents (e.g., *glycyrrhiza, aloe*, garlic, nigella *sativa*, rauwolfia, St John's wort, and valerian); enzymes (e.g., lipase, protease, amylase, lactase, lysozyme, and urokinase); humoral agents (e.g., prostaglandins, natural and synthetic, for example, PGE1, PGE2alpha, PGF2alpha, and the PGE1 analog misoprostol); psychic energizers (e.g., 3-(2-aminopropy)indole and 3-(2-aminobutyl)indole); nutritional agents; essential fatty acids; non-essential fatty acids; vitamins; minerals; and combinations thereof.

Any of the above-mentioned APIs may be incorporated in the pharmaceutical composition described herein in any suitable form, such as, for example, as a pharmaceutically acceptable salt, uncharged or charged molecule, molecular complex, solvate or hydrate, prodrug, and, if relevant, isomer, enantiomer, racemic mixture, and/or mixtures thereof. Furthermore, the API may be in any of its crystalline, semi-crystalline, amorphous, or polymorphous forms.

In one embodiment, the API present in the pharmaceutical composition may be susceptible to abuse. For example, the API may be an opioid analgesic agent, a stimulant agent, a sedative agent, a hypnotic agent, an antianxiolitic agent, or a muscle relaxing agent.

In another embodiment, the API present in the pharmaceutical composition may be a combination of an opioid analgesic and a non-opioid analgesic. Suitable opioid and non-opioid analgesics are listed above.

In exemplary embodiments, the API in the pharmaceutical composition may be an opioid analgesic. Exemplary opioid analgesics include oxycodone, oxymorphone, hydrocodone, hydromorphone, codeine, and morphine. In an exemplary embodiment, the API may be oxycodone hydrochloride. In another exemplary embodiment, the API may be oxymorphone hydrochloride.

The amount of API in the pharmaceutical composition can and will vary depending upon the active agent. In embodiments in which the API is an opioid analgesic, the amount of opioid in the pharmaceutical composition may range from about 2 mg to about 160 mg. In various embodiments, the amount of opioid in the pharmaceutical composition may range from about 2 mg to about 10 mg, from about 10 mg to about 40 mg, from about 40 mg to about 80 mg, or from about 80 mg to about 160 mg. In certain embodiments, the amount of opioid in the pharmaceutical composition may be about 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 45 mg, 50 mg, 60 mg, 70 mg, 80 mg, 100 mg, 120 mg, 140 mg, or 160 mg.

In embodiments in which the opioid is oxycodone hydrochloride, the total amount of oxycodone hydrochloride present in the pharmaceutical composition may range from about 2 mg to about 80 mg. In certain embodiments, the amount of oxycodone hydrochloride present in the pharmaceutical composition may range from about 2 mg to about 10 mg, from about 10 mg to about 30 mg, or from about 30 mg to about 80 mg. In preferred embodiments, the amount of oxycodone hydrochloride present in the pharmaceutical composition may be about 5 mg, about 10 mg, about 15 mg, about 20 mg, about 30 mg, about 40 mg, about 60 mg, or about 80 mg.

In embodiments in which the opioid is oxymorphone hydrochloride, the total amount of oxymorphone hydrochloride present in the pharmaceutical composition may range from about 2 mg to about 80 mg. In certain embodiments, the amount of oxymorphone hydrochloride present in the pharmaceutical composition may range from about 2 mg to about 10 mg, from about 10 mg to about 30 mg, or from about 30 mg to about 80 mg. In preferred embodiments, the amount of oxymorphone hydrochloride present in the pharmaceutical composition may be about 5 mg, about 10 mg, about 20 mg, about 30 mg, or about 40 mg.

(viii) Optional Excipients

In various embodiments, the pharmaceutical composition disclosed herein may further comprise at least one additional pharmaceutically acceptable excipient. Non-limiting examples of suitable excipients include binders, fillers, diluents, chelating agents, flavoring agents, coloring agents, taste masking agents, and combinations thereof.

In one embodiment, the excipient may be a binder. Suitable binders include, but are not limited to, starches, pregelatinized starches, gelatin, polyvinylpyrrolidone, cellulose, methyl cellulose, sodium carboxymethyl cellulose, ethyl cellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, peptides, and combinations thereof.

In another embodiment, the excipient may be a filler. Suitable fillers include carbohydrates, inorganic compounds, and polyvinylpyrrolidone. For example, the filler may be calcium sulfate, calcium phosphate, calcium silicate, microcrystalline cellulose, starch, modified starches, lactose, sucrose, mannitol, sorbitol, or combinations thereof.

In another embodiment, the excipient may include a diluent. Non-limiting examples of diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

In an alternate embodiment, the excipient may be a chelating agent. Non-limiting examples of suitable chelating agents include ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo) tetraacetic acid, 1,4,7,10-tetraazacyclodo-decane-N,N',N'', N'''-tetraacetic acid, 1,4,7,10-tetraaza-cyclododecane-N,N', N'''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid.

In a further embodiment, the excipient may be a flavoring agent. Flavoring agents may be chosen from synthetic flavor oils and flavoring aromatics and/or natural oils, extracts from plants, leaves, flowers, fruits, and combinations thereof.

In still another embodiment, the excipient may be a coloring agent. Suitable color additives include food, drug and cosmetic colors (FD&C), drug and cosmetic colors (D&C), or external drug and cosmetic colors (Ext. D&C).

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

The amount of excipient or excipients included in the pharmaceutical composition can and will vary depending upon the identity and amounts of the components of the pharmaceutical composition as detailed above.

(ix) Optional Film Coating

In some embodiments, the pharmaceutical composition may further comprise an optional film coating. Typically, the film coating comprises at least one water-soluble polymer, and the film coating does not affect the extended release or abuse deterrent properties of the pharmaceutical composition. The film coating may provide moisture protection, enhanced appearance, increased mechanical integrity, improved swallowability, improved taste, and/or masking of odors.

Film coatings are well known in the art, e.g., some are commercially available, e.g., under the tradename OPADRY®. Typically, a film coating comprises at least one water-soluble polymer and at least one plasticizer. Non-limiting examples of suitable polymers include hydroxypropylmethyl cellulose, hydroxypropyl cellulose, hydroxypropylethyl cellulose, ethyl cellulose, methyl cellulose, cellulose acetate phthalate, microcrystalline cellulose and carrageenan, acrylic polymers, polyvinyl alcohol, anionic and cationic polymers of methacrylic acid, copolymers of methacrylates, copolymers of acrylates and methacrylates, copolymers of ethacrylate and methyl methacrylate, polyvinylacetate phthalate, and shellac. Examples of suitable plasticizers include, without limit, triethyl citrate (TEC), acetyltriethyl citrate (ATEC), acetyl tri-n-butyl citrate (ATBC), dibutyl sebacate, diethyl phthalate, and triacetin. The film coating may optionally comprise additional agents such as a coloring agent, a filler, a flavoring agent, a taste-masking agent, a surfactant, an anti-tacking agent, and/or an anti-foaming agent. Suitable examples of these agents are well known in the art and/or are detailed above.

(x) Specific Embodiments

In one embodiment, the pharmaceutical composition comprises a glucomannan, a first polyethylene oxide having an average molecular weight of 100,000, and a second polyethylene oxide having an average molecular weight of 2,000,000. In another embodiment, the pharmaceutical composition comprises a glucomannan, a first polyethylene oxide having an average molecular weight of 100,000, a second polyethylene oxide having an average molecular weight of 7,000,000, and a hydrophilic gelling polymer (e.g., hydroxypropylmethylcellulose). In first polyethylene oxide having an average molecular weight of 100,000, a second polyethylene oxide having an average molecular weight of 2,000,000, and a plasticizer (e.g., vitamin E succinate). Each pharmaceutical composition further comprises an antioxidant and a lubricant.

In exemplary embodiments, the API is an opioid chosen from oxycodone, oxymorphone, hydrocodone, hydromorphone, codeine, or morphine. The pharmaceutical compositions, therefore, can be used for the treatment of pain conditions in subjects in need thereof. In general, the subject to be treated has been diagnosed as having a pain condition. As used herein, the term "pain" refers to the unpleasant sensory and emotional experience associated with actual or perceived tissue damage by a noxious stimulus. The pain may be acute or chronic pain. For example, the pain may be traumatic or inflammatory pain, which results from injury to non-neural tissue. Alternatively, the pain may be neuropathic pain, which results from injury to or inflammation of the central or peripheral nervous system. In general, the subject will be a human. However, other mammalian subjects may be treated with the pharmaceutical compositions disclosed herein.

(b) Dosage Forms

The physical form of the pharmaceutical composition disclosed herein can and will vary. In general, the pharmaceutical composition is a solid dosage form that is formulated for oral administration. The solid dosage form may be one of various solid dosage units. Non-limiting examples of suitable solid dosage units include tablets, compacts, pellets, caplets, pills, and capsules. Such dosage units may be prepared using conventional methods known to those in the field of pharmaceutical formulation and described in pertinent texts, e.g., in Gennaro, A. R., editor. "Remington: The Science & Practice of Pharmacy", 21st ed., 2006, Williams & Williams, and in the "Physician's Desk Reference", 66th ed., 2014, PDR Staff.

In specific embodiments, the solid dosage unit may be a tablet. Non-limiting types of tablets include coated tablets, uncoated tablets, compressed tablets, compacted tablets, molded tablets, layered tablets, bilayer tablets, extruded tablets, multiparticulate tablets, monolithic tablets, and matrix tablets.

In embodiments in which the solid dosage form is a tablet, the tablet generally has a friability of no greater than about 1.0%. In certain embodiments, the tablet may have a friability of less than about 1.0%, less than about 0.5%, less than about 0.3%, less than about 0.2%, less than about 0.1%, less than about 0.05%, or less than about 0.01%. In exemplary embodiments, the tablet has a friability of zero.

(c) In Vitro Release Properties of the Composition

The pharmaceutical composition disclosed herein is formulated such that the API in the composition is released over an extended period of time. For example, the total amount of API in the pharmaceutical composition may be released over a period of about 6 hours, over a period of about 12 hours, over a period of about 18 hours, or over a period of about 24 hours. In exemplary embodiments, the total amount of the API in the pharmaceutical composition may be released within about 8 hours to about 12 hours.

The in vitro dissolution of the API from the pharmaceutical composition disclosed herein may be measured using an approved USP procedure. For example, dissolution may be measured using an USP approved Type 2 paddle apparatus, at a paddle speed of 50 rpm or 100 rpm, and a constant temperature of 37±0.5° C. The dissolution test may be performed in the presence of 500 mL, 900 mL, or 1,000 mL of a suitable dissolution medium (e.g., having a pH from 1.0 to 6.8). Non-limiting examples of suitable dissolution media include water, phosphate buffer (pH 6.8), acetate buffer (pH 4.5), and 0.1 N HCl.

In various embodiments, the in vitro release of the API from the pharmaceutical composition is such that no more than about 50%, 60%, 70%, 80%, 90% or 95% of the API is released within about 6 hours. In additional embodiments, no more than about 80% of the API is released within about 6 hours. In still another embodiment, no more than about 50%, 60%, 70%, 80%, 90% or 95% of the API is released within about 8 hours.

(d) Abuse Deterrent Properties of the Composition

The solid dosage pharmaceutical compositions disclosed herein also have abuse deterrent features. The combination of the natural gum, low molecular weight polyalkylene oxide, and high molecular weight polyalkylene oxide imparts sufficient mechanical integrity (i.e., strength, hardness, elasticity, etc.) to the composition such that it is resistant to crushing, grinding, cutting, or pulverizing to form a powder comprising small particles. Additionally, the composition forms a viscous mixture or gel when in contact with a small volume of an aqueous solution.

The mechanical integrity of the pharmaceutical composition may be assessed by measuring the particle size distribution after crushing, grinding, or pulverizing the solid dosage composition in a suitable apparatus for a specified period of time. The pharmaceutical composition breaks into a plurality of particles having an average diameter of greater than about 250 microns when crushed, ground, or pulverized. The composition may be ground or milled in a coffee grinder, a spice grinder, a nut grinder, a coffee mill, a blender, a high-shear mill, a ball mill, a co-mill, a pill crusher, a tablet grinder, or another grinding/milling apparatus. In some embodiments, more than about 20%, more than about 30%, more than about 40%, more than about 50%, more than about 60%, more than about 70%, more than about 80%, or more than about 90% of the particles have an average diameter of greater than about 250 microns when the composition is subjected to 6 minutes of milling in a coffee grinder or high shear mill. Because the solid dosage pharmaceutical composition disclosed herein is resistant to forming a fine powder by crushing, grinding or pulverizing, it deters abuse by inhalation.

Alternatively, the mechanical integrity of the pharmaceutical composition may be accessed by measuring the breaking point or the breaking strength of the solid dosage composition. The breaking strength refers to the amount of applied force needed to compromise the integrity of the solid dosage form. The breaking point may be determined from a force profile of the composition. The force profile is a plot of force versus compression distance in which changes in the thickness of the solid dosage form are plotted as a function of increasing force applied to the solid dosage form (Haslam et al., Int. J. Pharmaceut., 1998, 173:233-242). The force profile may be generated using a Texture Analyzer model TA.XT. Plus (Texture Technologies Corp.), an Instron Universal Tester (Instron Engineering Corp.), or other suitable instrument. Force is applied diametrically to the solid dosage form and the compression distance is recorded. The breaking point exhibits itself as the point in the force profile plot at which the ascending line plateaus or descends in response to the application of increasing force. The breaking point may be expressed as force per compression distance.

Another method to determine the breaking point (or breaking strength) utilizes conventional hardness testers well known in the art. Appropriate models include, without limitation, Dr. Schleuniger® model 8M (Pharmatron Inc.), Varian model VK200 (Varian Medical Systems Inc.), or Sotax HT1 (Sotax Corp.). In this analysis, when the integrity of the solid dosage form is compromised, the instrument will stop compressing and report the force delivered to the dosage form at the breaking strength. In general, the pharmaceutical composition disclosed herein has a breaking strength of less than about 500 Newtons (N). In various embodiments, the breaking strength of the pharmaceutical composition is less than about 400 N, less than about 350 N, less than about 300 N, less than about 250 N, or less than about 200 N. As additional force is applied beyond the breaking point, the composition may continue to flatten or deform, which is indicative of plastic deformation.

An additional abuse deterrent property is that the pharmaceutical composition, whether whole, flattened, crushed, or broken into large particles, forms a viscous mixture or gel when in contact with a small volume (i.e., about 10 mL or less) of an aqueous solution at a variety of temperatures. The volume of the aqueous solution may range from about 1 mL to about 10 mL. For example, the volume may be about 1 mL, about 2 mL, about 3 mL, about 4 mL about 5 mL, about 6 mL, about 7 mL, about 8 mL, about 9 mL, or about 10 mL. Suitable aqueous solutions include water, alcohols such as ethanol, acids such as acetic acid, fruit juice, and mixtures of any of the foregoing. In certain embodiments, the temperature of the extraction may be about room temperature (i.e., about 23-25° C.), about 30° C., about 60° C., or about 90° C. The duration of the extraction may range from about 5 minutes to about 3 hours. In some embodiments, the duration of the extraction may be about 30 minutes or about 60 minutes. The resultant gel mixture has a high viscosity that prevents separation of the active ingredient from the viscous gel, provides a visual deterrence to injection abuse, and inhibits the gelled mixture from being drawn through an injection syringe needle. Consequently, the pharmaceutical compositions disclosed herein provide deterrence to abuse by extraction of the API and consequent injection of the extracted mixture.

(II) Process for Preparing Solid Dosage Pharmaceutical Compositions

Another aspect of the disclosure encompasses a process for preparing a solid dosage form of the pharmaceutical composition disclosed herein. The process comprises: (a) forming a mixture comprising at least one natural gum, at least one polyalkylene oxide having an average molecular weight of no more than 300,000, at least one polyalkylene oxide having an average molecular weight of at least 1,000,000, and at least one active pharmaceutical ingredient (API) or a pharmaceutically acceptable salt thereof; (b) forming the mixture into a solid dosage unit; and (c) and heating the solid dosage unit to form the solid dosage form of the pharmaceutical composition.

(a) Forming the Mixture

The first step of the process comprises forming a mixture comprising the components of the pharmaceutical composition, which are detailed above in section (I)(a). In general, the mixture comprises at least one API, least one natural gum, at least one polyalkylene oxide having an average molecular weight of no more than about 300,000, at least one polyalkylene oxide having an average molecular weight of at least 1,000,000, and one or more pharmaceutically acceptable excipients (such as, e.g., a lubricant). The components may be combined in any order or various combinations of the components may be premixed before being combined together.

The mixture comprising the components of the pharmaceutical composition may be formed by mixing, roller mixing, drum mixing, shear mixing, dry blending, chopping, milling, roller milling, granulating, dry granulating (e.g., slugging or roller compacting), wet granulating (e.g., fluid bed granulating, high shear granulating), and other mixing techniques known in the art. The mixture, therefore, may be a powder, a blend, or a granulate.

(b) Forming a Solid Dosage Unit

The process further comprises forming the mixture from step (a) into a solid dosage unit. Suitable solid dosage units are described above in section (I)(b). Means of forming solid dosage units are well known in the art. See, e.g., Gennaro, A. R., editor. "Remington: The Science & Practice of Pharmacy", 21st ed., 2006, Williams & Williams, and in the "Physician's Desk Reference", $66^{th}$ ed., 2014, PDR Staff. In specific embodiments, the solid dosage unit may be a tablet. The tablet may be a compression tablet, a molded tablet, a compacted tablet, or a pressed tablet. In exemplary embodiments, the tablet may be formed by direct compression. The shape of the tablet may vary. Non-limiting tablet shapes include round, oval, rectangular, and triangular. The size and mass of the tablet may vary. In various embodiments, the mass of the tablet may be range from about 100 mg to about 1000 mg. In exemplary embodiments, the mass of the tablet may range from about 200 mg to about 300 mg.

(c) Heating the Solid Dosage Unit

The process further comprises heating the solid dosage unit from step (b). This heating step cures any polymers in the composition that have softening temperatures below the selected temperature. The heating step also removes water from the solid dosage form, thereby protecting the API from oxidation. The solid dosage form prepared by the process disclosed herein has sufficient mechanical integrity such that it is resistant to crushing, cutting, milling, pulverizing, or other means of tampering.

In general, the heating step occurs at a temperature greater than about 50° C. For example, the solid dosage units may be heated to a temperature greater than about 50° C., greater than about 60° C., greater than about 70° C., greater than about 80° C., greater than about 90° C., or greater than about 100° C. In some embodiments, the heating occurs at a temperature of less than about 90° C. In exemplary embodiments, the temperature of the heating step may range from about 60° C. to about 90° C. In one embodiment, the temperature of the heating step may range from about 75° C. to about 85° C.

The duration of the heating step can and will vary depending upon the components of the pharmaceutical composition and the heating temperature. The duration of the heating step may range from about 10 minutes to about 10 hours. In some embodiments, the duration of the heating step may range from about 10 minutes to about 60 minutes, from about 1 hour to about 2 hours, from about 2 hours to about 3 hours, from about 3 hours to about 5 hours, or from about 5 to about 10 hours. In general, the higher the temperature, the shorter the duration of time for heating.

(d) Optionally Coating the Solid Dosage Unit

The process further comprises an optional step in which the solid dosage unit from step (b) or the solid dosage form from step (c) is coated with a film coating. Examples of suitable film coatings are detailed above in section (I)(a)(ix). The optional coating step prevents agglomeration or sticking among individual solid dosage forms and sticking between the solid dosage forms and the equipment. The film coating may be spray coated onto the solid dosage form. The spray coating system by be a bottom spray coating system, a top spray coating system, a tangential spray coating system, a pan coating system, or another suitable coating system.

Definitions

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about," particularly in reference to a given quantity, is meant to encompass deviations of plus or minus five percent.

As used herein, "abuse deterrent" refers to any property or feature of a pharmaceutical composition that lessens the potential for abuse of the active ingredient(s) in the composition.

Examples

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1: Preparation of Formulations 1 and 2

Two different oxycodone-containing preparations were prepared. The components listed in Table 1 were dry blended. The blends were compressed into tablets using a standard press. The tablets were placed in an aluminum pan and cured in a laboratory oven by heating at 80° C.

TABLE 1

Oxycodone Formulations 1 and 2

| Component | Formulation 1 | | Formulation 2 | |
| --- | --- | --- | --- | --- |
| | mg/tablet | % w/w | mg/tablet | % w/w |
| Oxycodone HCl | 40.00 | 16.05 | 40.00 | 14.19 |
| Glucomannan | 60.00 | 24.07 | 40.00 | 15.19 |
| PEO 100K | 91.63 | 36.76 | 124.00 | 43.98 |
| PEO 2M | 55.00 | 22.06 | — | 0 |
| PEO 7M | — | 0 | 55.00 | 19.51 |

TABLE 1-continued

Oxycodone Formulations 1 and 2

| | Formulation 1 | | Formulation 2 | |
|---|---|---|---|---|
| Component | mg/tablet | % w/w | mg/tablet | % w/w |
| HPMC K100M | — | 0 | 20.00 | 7.09 |
| Butylated hydroxytoluene | 0.15 | 0.06 | 0.15 | 0.05 |
| Magnesium stearate | 2.50 | 1.00 | 2.80 | 0.99 |
| Total | 249.28 | 100.00 | 281.95 | 100.00 |

Example 2: Preparation of Formulation 3

An oxymorphone formulation was prepared by blending the components listed in Table 2, compressing the mixture into tablets, and curing the tablets.

TABLE 2

Oxymorphone Formulation

| | Formulation 3 | |
|---|---|---|
| Component | mg/tablet | % w/w |
| Oxymorphone HCl | 40.00 | 13.96 |
| Glucomannan | 80.00 | 27.93 |
| PEO 100K | 123.55 | 43.13 |
| PEO 2M | 30.00 | 10.47 |
| Vitamin E succinate | 6.36 | 2.30 |
| EDTA | 3.64 | 1.27 |
| Magnesium stearate | 2.90 | 1.00 |
| Total | 286.45 | 100.00 |

What is claimed is:

1. A solid dosage form comprising an opioid or a pharmaceutically acceptable salt thereof, about 20-30% w/w of a glucomannan, about 35-45% w/w of a first polyethylene oxide having an average molecular weight of 100,000, about 18-24% w/w of a second polyethylene oxide having an average molecular weight of 2,000,000, about 0.01-0.3% w/w of an antioxidant, about 1-3% w/w of a lubricant, and an optional film coating.

2. The solid dosage form of claim 1, wherein the solid dosage form releases no more than about 80% of the opioid within about 6 hours using an USP in vitro release procedure.

3. The solid dosage form of claim 1, wherein the solid dosage form has abuse deterrent properties.

4. The solid dosage form of claim 3, wherein the solid dosage form deters abuse by breaking into a plurality of particles having an average diameter of greater than about 250 microns when crushed, ground, or pulverized.

5. The solid dosage form of claim 3, wherein the solid dosage form deters abuse by forming a viscous gel upon contact with about 10 mL or less of an aqueous solution.

6. The solid dosage form of claim 1, wherein the opioid is oxycodone, oxymorphone, hydrocodone, hydromorphone, codeine, or morphine.

7. A solid dosage form comprising an opiate or a pharmaceutically acceptable salt thereof, about 10-20% w/w of a glucomannan, about 30-50% w/w of a first polyethylene oxide having an average molecular weight of 100,000, about 18-24% w/w of a second polyethylene oxide having an average molecular weight of 7,000,000, about 5-20% w/w of a hydrophilic gelling polymer other than a polyalkylene oxide, about 0.02-0.3% w/w of an antioxidant, about 1-3% w/w of a lubricant, and an optional film coating.

8. The solid dosage form of claim 7, wherein the solid dosage form releases no more than about 80% of the opioid within about 6 hours using an USP in vitro release procedure.

9. The solid dosage form of claim 7, wherein the solid dosage form has abuse deterrent properties.

10. The solid dosage form of claim 9, wherein the solid dosage form deters abuse by breaking into a plurality of particles having an average diameter of greater than about 250 microns when crushed, ground, or pulverized.

11. The solid dosage form of claim 9, wherein the solid dosage form deters abuse by forming a viscous gel upon contact with about 10 mL or less of an aqueous solution.

12. The solid dosage form of claim 7, wherein the opioid is oxycodone, oxymorphone, hydrocodone, hydromorphone, codeine, or morphine.

13. A solid dosage form comprising an opiate or a pharmaceutically acceptable salt thereof, about 20-30% w/w of a glucomannan, about 30-50% w/w of a first polyethylene oxide having an average molecular weight of 100,000, about 9-11% A w/w of a second polyethylene oxide having an average molecular weight of 2,000,000, about 1-3% w/w of a plasticizer chosen from vitamin E succinate or vitamin E palmitate, about 1-3% w/w of a lubricant, and an optional film coating.

14. The solid dosage form of claim 13, wherein the solid dosage form releases no more than about 80% of the opioid within about 6 hours using an USP in vitro release procedure.

15. The solid dosage form of claim 13, wherein the solid dosage form has abuse deterrent properties.

16. The solid dosage form of claim 15, wherein the solid dosage form deters abuse by breaking into a plurality of particles having an average diameter of greater than about 250 microns when crushed, ground, or pulverized.

17. The solid dosage form of claim 15, wherein the solid dosage form deters abuse by forming a viscous gel upon contact with about 10 mL or less of an aqueous solution.

18. The solid dosage form of claim 13, wherein the opioid is oxycodone, oxymorphone, hydrocodone, hydromorphone, codeine, or morphine.

* * * * *